(12) United States Patent
Kwak et al.

(10) Patent No.: US 7,214,793 B2
(45) Date of Patent: May 8, 2007

(54) METHOD OF PREPARING 10H-DIBENZO[B,F][11,4]THIAZEPIN-11-ONE

(75) Inventors: Byong-Sung Kwak, Daejeon (KR); Ki-Nam Chung, Daejeon (KR); Ki-Ho Koh, Daejeon (KR); Hee-Jun Hwang, Daejeon (KR)

(73) Assignee: SK Corporation, Seoul (KR)

( * ) Notice: Subject to any disclaimer, the term of this patent is extended or adjusted under 35 U.S.C. 154(b) by 129 days.

(21) Appl. No.: 10/533,052

(22) PCT Filed: Nov. 26, 2003

(86) PCT No.: PCT/KR03/02579

§ 371 (c)(1),
(2), (4) Date: Apr. 26, 2005

(87) PCT Pub. No.: WO2004/047722

PCT Pub. Date: Jun. 10, 2004

(65) Prior Publication Data

US 2007/0066589 A1    Mar. 22, 2007

(30) Foreign Application Priority Data

Nov. 28, 2002   (KR) ...................... 10-2002-0074691

(51) Int. Cl.
*C07D 281/16*   (2006.01)

(52) U.S. Cl. ..................................................... 540/488
(58) Field of Classification Search ................. 540/488
See application file for complete search history.

(56) References Cited

FOREIGN PATENT DOCUMENTS

| EP | 0240228 | 10/1987 |
|---|---|---|
| EP | 0282236 | 9/1988 |

*Primary Examiner*—Bruck Kifle
(74) *Attorney, Agent, or Firm*—Abelman, Frayne & Schwab

(57) ABSTRACT

Disclosed is a method of preparing 10H-dibenzo[b,f][1,4] thiazepin-11-one, including reacting dithiosalicylic acid with 1-chloro-2-nitrobenzene in a basic aqueous solution in the presence or absence of a reducing agent, to prepare 2-(2-nitrophenylsulfuryl)benzoic acid; subjecting the 2-(2-nitrophenylsulfuryl)benzoic acid to nitro group reduction in the presence of hydrogen, a solvent and a heterogeneous metal catalyst, to prepare 2-(2-aminophenylsulfuryl)benzoic acid; and directly cyclizing the 2-(2-aminophenylsulfuryl) benzoic acid in an organic solvent in the presence or absence of an acid catalyst. The method according to the present invention is economical due to the use of the inexpensive starting material, and also environmentally friendly and efficient by minimizing the use of the organic solvent and performing direct cyclization without the activation of carboxylic acid.

13 Claims, No Drawings

METHOD OF PREPARING 10H-DIBENZO[B,F][11,4]THIAZEPIN-11-ONE

TECHNICAL FIELD

The present invention relates to a method of preparing 10H-dibenzo[b,f][1,4]thiazepin-11-one represented by Formula 1. More specifically, the present invention relates to an environmentally friendly, economical and efficient method of preparing 10H-dibenzo[b,f][1,4]thiazepin-11-one, by reacting dithiosalicylic acid with 1-chloro-2-nitrobenzene in a basic aqueous solution, followed by nitro group reduction using a heterogeneous metal catalyst and then direct cyclization without activation of carboxylic acid, therefore resulting in minimized use of an organic solvent:

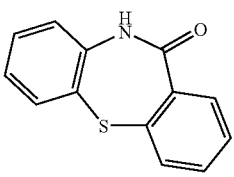

Formula 1

BACKGROUND ART

In general, 10H-dibenzo[b,f][1,4]thiazepin-11-one is applied as an intermediate to formulate medicines for treatment of psychiatric disorders, and is typically produced as follows.

That is, 1-chloro-2-nitrobenzene reacts with thiophenol, to prepare 2-nitrodiphenylsulfide, after which a nitro group of the prepared compound is reduced to an amino group. The reduced amino group is activated to isocyan using phosgene, which is then cyclized by use of aluminum trichloride, to give 10H-dibenzo[b,f][1,4]thiazepin-11-one, which is disclosed in Helv. Chim Acta, 48, 336 (1965). However, the above method is disadvantageous in terms of difficulties of commercial production, due to the use of hazardous phosgene for the cyclization.

Also, in the above literature (Helv. Chim Acta, 48, 336 (1965)), there is disclosed the preparation of 10H-dibenzo[b,f][1,4]thiazepin-11-one by reacting 2-chloronitrobenzene with thiosalicylic acid methyl ester. However, this method suffers from the use of expensive thiosalicylic acid methyl ester, thus negating economic benefits. In addition, since all the reactions take place in the organic solvent, the above method is environmentally unfriendly.

Likewise, a method of preparing 10H-dibenzo[b,f][1,4]thiazepin-11-one by activating 2-aminodiphenylsulfide by use of chloroformic acid phenyl ester is disclosed in European Patent Laid-open Publication Nos. 0240228 and 028236. However, the above method is environmentally unfriendly, because excessive amounts of acidic wastewater are generated by using polyphosphoric acid, which is a strong acid, as the solvent for the cyclization. Further, it is difficult to commercially produce the desired product.

Disclosed in J. Med. Chem. 44, 372–389, 2001, a method of preparing 10H-dibenzo[b,f][1,4]thiazepin-11-one starting from 2-bromonitrobenzene and thiosalicyiic acid is difficult to commercially apply, due to the use of hazardous tin chloride upon the reduction of the nitro group.

DISCLOSURE OF THE INVENTION

Therefore, it is an object of the present invention to provide a method of preparing 10H-dibenzo[b,f][1,4]thiazepin-11-one, which is economical and efficient by using inexpensive dithiosalicylic acid and also environmentally friendly by minimizing the use of an organic solvent.

BEST MODE FOR CARRYING OUT THE INVENTION

Based on the present invention, 10H-dibenzo[b,f][1,4]thiazepin-11-one represented by Formula 1 is prepared by reacting dithiosalicylic acid represented by Formula 2 with 1-chloro-2-nitrobenzene in a basic aqueous solution in the presence or absence of a reducing agent, to prepare 2-(2-nitrophenylsulfuryl)benzoic acid represented by Formula 3; subjecting the 2-(2-nitrophenylsulfuryl)benzoic acid represented by Formula 3 to nitro group reduction in the presence of hydrogen, a solvent and a heterogeneous metal catalyst, to prepare 2-(2-aminophenylsulfuryl)benzoic acid represented by Formula 4; and directly cyclizing the 2-(2-aminophenylsulfuryl)benzoic acid represented by Formula 4 in an organic solvent in the presence or absence of an acid catalyst:

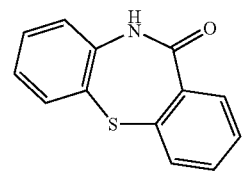

Formula 1

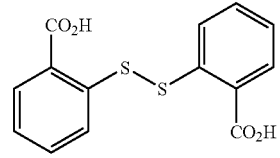

Formula 2

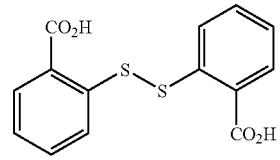

Formula 3

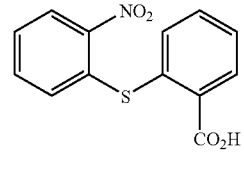

Formula 4

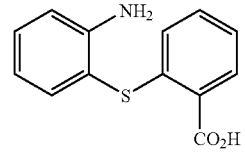

Specifically, dithiosalicylic acid represented by Formula 2 reacts with 1-chloro-2-nitrobenzene in the basic aqueous solution, to obtain 2-(2-nitrophenylsulfuryl)benzoic acid represented by Formula 3.

As such, 1-chloro-2-nitrobenzene is used in an amount of 2–3 equivalents, and preferably, 2–2.2 equivalents, based on 1 equivalent of dithiosalicylic acid represented by Formula 2. If the amount of 1-chloro-2-nitrobenzene is less than 2 equivalents, the reaction is not completely terminated. Meanwhile, if the amount exceeds 3 equivalents, economic benefits do not occur.

A base for use in the basic aqueous solution is selected from the group consisting of sodium hydroxide, potassium hydroxide, lithium hydroxide, sodium carbonate, potassium carbonate, and sodium bicarbonate. In particular, sodium hydroxide or potassium hydroxide is preferably used. Further, sodium hydroxide is the most preferable. In this case, the base is used in an amount of 4–5 equivalents, and preferably, 4–4.2 equivalents. If the base is used in the amount less than 4 equivalents, a conversion efficiency decreases upon the reaction. On the other hand, if the amount exceeds 5 equivalents, economic benefits are lost.

The reaction of dithiosalicylic acid with 1-chloro-2-nitrobenzene is performed at 50–100° C., and preferably, 80–100° C. The reaction temperature lower than 50° C. results in a decreased reaction rate, which is inefficient.

Upon the above reaction, a reducing agent may be used to increase the reaction rate. However, even though the reducing agent is not used, the reaction may naturally take place. In such a case, the usable reducing agent includes sodium borohydride, sodium hyposulfite, zinc, magnesium or hydrazine.

In cases of using a phase transfer catalyst in the above reaction, the reaction rate may be slightly increased, but is not largely affected by such a catalyst. The usable phase transfer catalyst is selected from the group consisting of benzyltrimethylammonium chloride, benzyltriethylammonium chloride, benzyltributylammonium chloride, tetramethylammonium chloride, tetraethylammonium chloride, tetrabutylammonium chloride, benzyltrimethylammonium bromide, benzyltriethylammonium bromide, benzyltributylammonium bromide, tetramethylammonium bromide, tetraethylammonium bromide, tetrabutylammonium bromide, benzyltrimethylammonium iodide, benzyltriethylammonium iodide, benzyltributylammonium iodide, tetramethylammonium iodide, tetraethylammonium iodide, tetrabutylammonium iodide, benzyltrimethylammonium hydrosulfate, benzyltriethylammonium hydrosulfate, benzyltributylammonium hydrosulfate, tetramethylammonium hydrosulfate, tetraethylammonium hydrosulfate, and tetrabutylammonium hydrosulfate.

Thereafter, the produced 2-(2-nitrophenylsulfuryl)benzoic acid is subjected to nitro group reduction in the presence of hydrogen, the solvent and the heterogeneous metal catalyst, to obtain 2-(2-aminophenylsulfuryl)benzoic acid represented by Formula 4.

The catalyst used for the nitro group reduction includes a metal per se, or a supported metal to a support, in which the metal is exemplified by Raney-nickel (Raney-Ni), ruthenium (Ru), palladium (Pd), platinum (Pt), and rhodium (Rh). In particular, Raney-nickel is preferable. In addition, the support is selected from among inorganic oxides, such as alumina, silica, zeolite and molecular sieve.

The heterogeneous metal catalyst is used in an amount of 2–30 wt %, and preferably, 5–20 wt %, based on total reactants. When the amount of the heterogeneous metal catalyst is less than 2 wt %, both the activity of the nitro group reduction and the selectivity of 2-(2-aminophenylsulfuryl)benzoic acid decrease. On the other hand, if the amount exceeds 30 wt %, economic benefits do not occur due to the use of the expensive metal.

The solvent suitable for the nitro group reduction is selected from the group consisting of water ($H_2O$), methyl alcohol, ethyl alcohol, n-propyl alcohol, and iso-propyl alcohol. Preferably, the solvent is water or methyl alcohol. Further, 2-(2-nitrophenylsulfuryl)benzoic acid is used in an amount of 1–50 wt %, and preferably, 5–40 wt %, based on the total reactants. In such a case, the use of the 2-(2-nitrophenylsulfuryl)benzoic acid smaller than 1 wt % results in excessive use of the solvent, thus decreasing productivity. Whereas, the use of the amount larger than 50 wt % leads to a decreased reactivity.

Through the nitro group reduction under 10–1,000 psig, hydrogen is dissolved. Further, the reduction is performed at 1–200° C. for 1–14 hours. It is preferred that the above reaction is carried out at 10–170° C. under 100–900 psig.

10H-dibenzo[b,f][1,4]thiazepin-11-one represented by Formula 1 is produced by directly cyclizing 2-(2-aminophenylsulfuryl)benzoic acid represented by Formula 4 in the organic solvent in the presence or absence of the acid catalyst, without activation of carboxylic acid.

Upon the cyclization, the acid catalyst functions to further increase the reaction rate. The usable acid catalyst is exemplified by sulfuric acid, phosphoric acid, nitric acid, p-toluenesulfonic acid, or benzenesulfonic acid. Preferably, sulfuric acid or phosphoric acid is used. The acid catalyst is used in the amount of 0.1–5 wt %, and preferably, 0.5–2 wt %, based on the total reactants. If the amount of the acid catalyst is less than 0.1 wt %, the reaction rate decreases. Whereas, if the amount is larger than 5 wt %, economic benefits are difficult to maintain. Although the reaction may be performed even in the absence of the acid catalyst, the reaction rate drastically decreases if so.

The cyclization is carried out at 50–200° C., and preferably 100–160° C. If the cyclization temperature is lower than 50° C., the cyclization does not take place well. Meanwhile, if the temperature is higher than 200° C., economic benefits negate.

The organic solvent suitable for the cylization includes benzene, toluene, or xylene. In particular, xylene is preferable. Moreover, 2-(2-aminophenylsulfuryl)benzoic acid is used in the amount of 1–50 wt %, and preferably 15–30 wt %, based on the total reactants. If the amount of 2-(2-aminophenylsulfuryl)benzoic acid is less than 1 wt %, productivity decreases due to the excessive use of the solvent. Whereas, if the amount exceeds 50 wt %, commercial production is restricted, attributable to the stirring problems.

As mentioned above, the method of preparing 10H-dibenzo[b,f][1,4]thiazepin-11-one, including the reaction of dithiosalicylic acid with 1-chloro-2-nitrobenzene in the basic aqueous solution, followed by the nitro group reduction and then direct cyclization without the activation of carboxylic acid, is characterized by minimizing the use of the organic solvent, and thus regarded as environmentally friendly, economical, and efficient method.

Having generally described this invention, a further understanding can be obtained by reference to specific examples which are provided herein for purposes of illustration only and are not intended to be limiting unless otherwise specified.

EXAMPLE 1

Into a 0.5 L reactor equipped with a stirrer and a refluxing unit, dithiosalicylic acid (50 g, 0.163 mol) and sodium hydroxide (26.1 g, 0.653 mol) were placed, and then dissolved in 175 ml of water. Subsequently, the reaction solution was added with 1-chloro-2-nitrobenzene (54 g, 0.343 mol) and refluxed at 100–105° C. for five hours. The resultant reaction was extracted with ethyl acetate (200 ml×2), thus removing unreactant 1-chloro-2-nitrobenzene. The aqueous solution layer was neutralized with an aqueous hydrochloric acid solution and then extracted with ethyl acetate (200 ml×2). The extracted ethyl acetate solution was dried over anhydrous magnesium sulfide, and the solvent was removed under reduced pressure. Thusly obtained product was dried under reduced pressure, to give 2-(2-nitrophenylsulfuryl)benzoic acid (80.7 g).

EXAMPLES 2 TO 4

In a 1.0 L reactor equipped with a stirrer and a refluxing unit, 90 g of 2-(2-nitrophenylsulfuryl)benzoic acid obtained in Example 1 was dissolved in 270 g of water. As a heterogeneous metal catalyst, 18 g of Raney-nickel was used. Further, the amount of 2-(2-nitrophenylsulfuryl)benzoic acid was adjusted in 20 wt %, based on total reactants.

During the reaction, pressure affecting the dissolution of hydrogen, temperature and time were variously changed. The results according to the change of reaction conditions are shown in Table 1, below. The reaction product was gathered every three hours and analyzed with liquid chromatography. The reaction product, 2-(2-aminophenylsulfuryl)benzoic acid, was confirmed with $^1$H-NMR (CDCl$_3$, 500 MHZ).

TABLE 1

| Ex. No. | Temp. (0° C.) | Pressure (psig) | Time (hr) | Conversion (%) | Selectivity (%)* |
|---------|---------------|-----------------|-----------|----------------|------------------|
| 2 | 50 | 145 | 13.5 | 46 | 68.9 |
| 3 | 100 | 450 | 3 | 100 | 98 |
| 4 | 150 | 450 | 3 | 100 | 96 |

*Reaction selectivity of 2-(2-aminophenylsulfuryl)benzoic acid

EXAMPLES 5 AND 6

In a 0.5 L reactor equipped with a stirrer and a refluxing unit, 20 g of 2-(2-nitrophenylsulfuryl)benzoic acid obtained in Example 1 was dissolved in a solvent. The reaction conditions were the same as Example 2, with the exception that the reaction time, the solvent and the using amount of the solvent were changed as shown in the following Table 2.

TABLE 2

| Ex. No. | Solvent | Amount (wt %)* | Time (hr) | Conversion (%) | Selectivity (%) |
|---------|---------|----------------|-----------|----------------|-----------------|
| 5 | Water | 10 | 3 | 100 | 98 |
| 6 | Methanol | 20 | 6 | 100 | 97 |

*Amount of 2-(2-nitrophenylsulfuryl)benzoic acid based on total reactants

EXAMPLE 7

2-(2-aminophenylsulfuryl)benzoic acid (30 g, 0.122 mol) obtained in Example 5, sulfuric acid (0.15 g), and xylene (100 ml) were placed into a 0.5 L reactor, and then refluxed at 145–150° C. for six hours. The resultants were cooled to room temperature, after which the produced solid was filtered and washed with methanol. The solid was dried under reduced pressure, to give 10H-dibenzo[b,f][1,4]thiazepin-11-one (25.3 g), as the yield of 91%.

INDUSTRIAL APPLICABILITY

As described hereinbefore, the present invention provides a method of preparing 10H-dibenzo[b,f][1,4]thiazepin-11-one, characterized in that inexpensive dithiosalicylic acid reacts with 1-chloro-2-nitrobenzene in a basic aqueous solution, following by nitro group reduction in water or alcohol solvent in the presence of a heterogeneous metal catalyst. Thereby, the use of an unnecessary organic solvent is excluded, and thus the method of the present invention is both economical and environmentally friendly. Further, the cyclization is directly performed without the activation of carboxylic acid, thereby effectively solving conventional difficulties of commercial production due to the use of a hazardous compound for the cyclization and larger amounts of waste acids.

Although the preferred embodiments of the present invention have been disclosed for illustrative purposes, those skilled in the art will appreciate that various modifications, additions and substitutions are possible. Therefore, it should be understood that within the scope of the appended claims, the invention may be practiced otherwise than as specifically described.

The invention claimed is:

1. A method of preparing 10H-dibenzo[b,f][1,4]thiazepin-11-one represented by Formula 1, comprising the steps of:
   (a) reacting dithiosalicylic acid represented by Formula 2 with 1-chloro-2-nitrobenzene in a basic aqueous solution in the presence or absence of a reducing agent, to prepare 2-(2-nitrophenylsulfuryl)benzoic acid represented by Formula 3;
   (b) subjecting the 2-(2-nitrophenylsulfuryl)benzoic acid represented by Formula 3 to nitro group reduction in the presence of hydrogen gas, a solvent and a heterogeneous metal catalyst, to prepare 2-(2-aminophenylsulfuryl)benzoic acid represented by Formula 4; and
   (c) directly cyclizing the 2-(2-aminophenylsulfuryl)benzoic acid represented by Formula 4 in an organic solvent in the presence or absence of an acid catalyst:

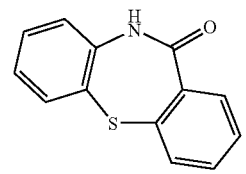

Formula 1

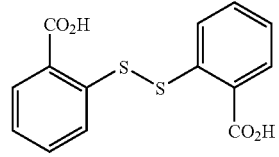

Formula 2

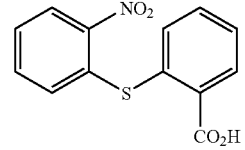

Formula 3

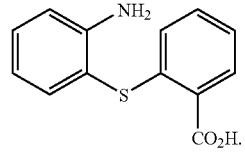

Formula 4

2. The method as defined in claim 1, wherein the step (a) is performed at 50–100° C., in which 1-chloro-2-nitrobenzene is used in an amount of 2–3 equivalents, based on 1 equivalent of dithiosalicylic acid.

3. The method as defined in claim 1, wherein a base for use in the basic aqueous solution is selected from the group consisting of sodium hydroxide, potassium hydroxide, lithium hydroxide, sodium carbonate, potassium carbonate, and sodium bicarbonate, and is used in an amount of 4–5 equivalents.

4. The method as defined in claim 1, wherein the reducing agent is selected from the group consisting of sodium borohydride, sodium hyposulfite, zinc, magnesium, and hydrazine.

5. The method as defined in claim 1, wherein the step (b) is performed at 1–200° C. under pressure of 10–1,000 psig for 1–14 hours.

6. The method as defined in claim 1, wherein the solvent used in the step (b) is selected from the group consisting of water, methyl alcohol, ethyl alcohol, n-propyl alcohol, and iso-propyl alcohol.

7. The method as defined in claim 1, wherein the 2-(2-nitrophenylsulfuryl)benzoic acid in the step (b) is used in an amount of 1–50 wt %, based on total reactants.

8. The method as defined in claim 1, wherein the heterogeneous metal catalyst comprises a metal selected from the group consisting of Raney-nickel (Raney-Ni), ruthenium (Ru), palladium (Pd), platinum (Pt), and rhodium (Rh), and is used in an amount of 2–30 wt %, based on the total reactants.

9. The method as defined in claim 1, wherein the heterogeneous metal catalyst comprises a metal supported to a support, and is used in an amount of 2–30 wt %, based on the total reactants, and the metal being selected from the group consisting of Raney-nickel (Raney-Ni), ruthenium (Ru), palladium (Pd), platinum (Pt), and rhodium (Rh), and the support being selected from the group consisting of alumina, silica, zeolite, and molecular sieve.

10. The method as defined in claim 1, wherein the step (c) is performed at 50–200° C.

11. The method as defined in claim 1, wherein the acid catalyst is selected from the group consisting of sulfuric acid, phosphoric acid, nitric acid, p-toluene sulfonic acid, and benzene sulfonic acid, and is used in the amount of 0.1–5 wt %, based on the total reactants.

12. The method as defined in claim 1, wherein the organic solvent in the step (c) is selected from the group consisting of benzene, toluene, and xylene.

13. The method as defined in claim 1, wherein the 2-(2-aminophenylsulfuryl)benzoic acid is used in an amount of 1–50 wt %, based on the total reactants.

* * * * *